United States Patent
Keel et al.

(10) Patent No.: US 8,280,523 B2
(45) Date of Patent: Oct. 2, 2012

(54) SYSTEM AND METHOD FOR MONITORING DIASTOLIC FUNCTION USING AN IMPLANTABLE MEDICAL DEVICE

(75) Inventors: Allen Keel, San Jose, CA (US); Steve Koh, South Pasadena, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 953 days.

(21) Appl. No.: 12/341,355

(22) Filed: Dec. 22, 2008

(65) Prior Publication Data

US 2010/0161006 A1    Jun. 24, 2010

(51) Int. Cl.
*A61N 1/36* (2006.01)
*A61N 1/378* (2006.01)

(52) U.S. Cl. .......................................... 607/62; 607/28
(58) Field of Classification Search ............... 607/62, 607/17, 27, 28, 9
See application file for complete search history.

(56) References Cited

U.S. PATENT DOCUMENTS

| | | | |
|---|---|---|---|
| 6,512,952 B2 | 1/2003 | Stahmann et al. | |
| 6,628,988 B2 | 9/2003 | Kramer et al. | |
| 6,643,546 B2 | 11/2003 | Mathis et al. | |
| 7,225,015 B1 | 5/2007 | Min et al. | |
| 2004/0077962 A1 | 4/2004 | Kroll | |
| 2004/0106954 A1 | 6/2004 | Whitehurst et al. | |

OTHER PUBLICATIONS

Steinhaus et al., "The information content of the cardiac electrogram at the stimulus site," Annual International Conference of the IEEE Engineering in Medicine and Biology Society, vol. 12, No. 2, pp. 607-609, 1990.

Okin et W., "Electrocardiographic strain pattern and prediction of new-onset congestive heart failure in hypertensive patients: the Losartan Intervention for Endpoint Reduction in Hypertension (LIFE) study." Circulation 2006; 113; 67-73; Published online before print Dec. 19, 2005, doi: 10.1161/CIRCULATIONAHA.105.569491.

*Primary Examiner* — Carl H. Layno
*Assistant Examiner* — Jon-Eric C. Morales
(74) *Attorney, Agent, or Firm* — Steven M Mitchell; Theresa A Raymer

(57) ABSTRACT

Diastolic function is monitored within a patient using a pacemaker or other implantable medical device. In one example, the implantable device uses morphological parameters derived from the T-wave evoked response waveform as proxies for ventricular relaxation rate and ventricular compliance. In particular, the magnitude of the peak of the T-wave evoked response is employed as a proxy for ventricular compliance. The maximum slew rate of the T-wave evoked response following its peak is employed as a proxy for ventricular relaxation. A metric is derived from these proxy values to represent diastolic function. The metric is tracked over time to evaluate changes in diastolic function. In other examples, specific values for ventricular compliance and ventricular relaxation are derived for the patient based on the T-wave evoked response parameters.

27 Claims, 7 Drawing Sheets

SYSTEM AND METHOD FOR MONITORING DIASTOLIC FUNCTION USING AN IMPLANTABLE MEDICAL DEVICE

FIELD OF THE INVENTION

The invention generally relates to implantable medical devices, such as pacemakers or implantable cardioverter-defibrillators (ICDs), and in particular to techniques for monitoring or evaluating diastolic function within patients in which such devices are implanted so as to detect diastolic dysfunction and diastolic heart failure.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive.

One particular form of heart failure is diastolic heart failure (DHF) wherein systolic function is generally preserved but diastolic function is compromised, i.e. there is a significant degree of diastolic dysfunction. Diastolic dysfunction refers to an abnormality in the ability of the heart to fill during diastole, which is the phase of the cardiac cycle when the ventricles relax and fill with blood prior to contraction.

Current methods (such as echocardiography) to measure diastolic function within patients so as to detect diastolic dysfunction and DHF are not being routinely used clinically, especially on asymptomatic patients. Accordingly, diastolic dysfunction can remain undetected for years within a patient until symptoms develop.

Hence, there is a need to provide improved techniques for monitoring or evaluating diastolic function within a patient. Many patients with heart failure that have, or are susceptible to, diastolic dysfunction already have pacemakers, ICDs or CRT-Ds implanted therein (or are candidates for such devices.) (A CRT-D is a cardiac resynchronization therapy device with defibrillation capability.) Accordingly, it is desirable to provide such devices with the capability to monitor diastolic function and to detect and track diastolic dysfunction within the patient, such that suitable warning signals can be generated or other appropriate actions can be taken. The invention is generally directed to these ends.

SUMMARY OF THE INVENTION

In accordance with exemplary embodiments of the invention, techniques are provided for monitoring or evaluating diastolic function within a patient using an implantable medical device such as a pacemaker or ICD. Briefly, parameters representative of ventricular repolarization evoked response (ER) morphology are detected within the patient, such as the T-wave ER peak magnitude and the post-peak maximum T-wave ER slew rate. Then parameters representative of diastolic function are determined from the ventricular repolarization ER morphological parameters, such as parameters representative of ventricular relaxation rate or ventricular compliance. One or more functions of the implantable device are then controlled based on the parameters representative of diastolic function, such as by controlling the storage of diagnostic information pertaining to diastolic function, controlling the generation of warning signals indicative of the onset of diastolic dysfunction, or controlling the delivery of therapy in response to diastolic dysfunction.

Note that the T-wave is the electrical cardiac signal associated with the repolarization, i.e. relaxation, of the ventricles. The T-wave follows a QRS-complex (sometimes called an R-wave), which is the electrical cardiac signal associated with the depolarization, i.e. contraction, of the ventricles. QRS-complexes and T-waves can be "intrinsic," i.e. the ventricles of the heart contract naturally in response to native electrical pacing signals arising within the heart. Alternatively, QRS-complexes and T-waves can be "paced," i.e. the ventricles of the heart contract in response to artificial electrical pacing signals applied to the heart, such as V-pulses applied to the ventricles by the pacing/sensing leads of a pacemaker. When the QRS-complexes and T-waves arise in response to artificial pacing pulses, the electrical response is referred to as an "evoked response." Accordingly, the "T-wave ER" refers to the repolarization portion of an evoked electrical response of the ventricles triggered by an artificial pacing pulse.

In general, ER waveforms provide information about myocardial stretch, contractility, and conduction velocity. It is believed that the T-wave portion of the ER provides information about diastolic filling and hence is useful in monitoring diastolic function. In particular, selected T-wave ER parameters may be used to evaluate ventricular relaxation and ventricular compliance, from which a measure of diastolic function can be derived. More specifically, the ventricular relaxation rate of a patient can be derived from the slew rate (i.e. slope) of the T-wave ER. Insofar as ventricular compliance is concerned, studies have shown that the peak amplitude of the ER "R-wave" is correlated with ventricular wall thickness. See, Steinhaus et al., "The information content of the cardiac electrogram at the stimulus site," Annual International Conference of the IEEE Engineering in Medicine and Biology Society, vol. 12, no. 2, pp. 607-609, 1990. From this observation and the fact that LV hypertrophy and compliance are intertwined, it is believed that ventricular compliance can be derived from the peak magnitude of the T-wave ER. Regardless of the precise medical explanation for its efficacy, T-wave ER parameters may be advantageously used to estimate ventricular relaxation and compliance. By implementing these functions within a pacer/ICD, a convenient ambulatory monitoring method is thereby provided.

In one example, the implanted device detects the maximum post-peak T-wave ER slew rate of the patient based on the maximum rate of change of the magnitude of a T-wave ER signal following the peak of the T-wave signal. The device then uses the maximum post-peak T-wave ER slew rate as a proxy for ventricular relaxation rate. That is, the higher the maximum post-peak T-wave ER slew rate, the higher the ventricular relaxation rate. Additionally or alternatively, the device can estimate the actual ventricular relaxation rate for the patient by exploiting a predetermined correlation between the maximum post-peak T-wave ER slew rate and the ventricular relaxation rate within the patient. For example, the device calculates:

$$\text{Ventricular Relaxation Rate} = f_1(T\text{-wave\_ER\_SlewRate})$$

where T-wave_ER_SlewRate represents the maximum post-peak T-wave ER slew rate of the patient and $f_1(\ )$ is a predetermined function for relating the maximum post-peak T-wave ER slew rate of the patient to the ventricular relaxation rate of the patient. Depending upon the desired degree of accuracy to be achieved in relating one to the other, $f_1(\ )$ can be a first-order function, a second-order function, an exponential function, etc. The function (and any of its adjustable coefficients) can be predetermined by comparing actual values of ventricular relaxation rates obtained via echocardiography to actual values of T-wave_ER_Slew Rate. In one particular example, $f_1(\ )=1-\exp(-a_1*T\text{-wave\_ER\_SlewRate})$ where $a_1$ is a predetermined coefficient calibrated using echocardiography. In some examples, the coefficient $a_1$ is calibrated to specifically relate the slew rate to the LV relaxation rate of the patient so that LV relaxation is thereby specifically estimated.

Also, in the example, the implanted device detects the T-wave ER peak magnitude of the patient based on the absolute magnitude of the T-wave ER signal at the peak of the T-wave signal. The device then uses the T-wave ER peak magnitude as a proxy for ventricular compliance. That is, the higher the peak magnitude, the better the ventricular compliance. Additionally or alternatively, the device estimates the actual ventricular compliance value for the patient by exploiting a predetermined correlation between T-wave ER peak magnitude and ventricular compliance within the patient. For example, the device calculates:

$$\text{Ventricular Compliance} = f_2(1/T\text{-wave\_ER\_Peak\_Mag}),$$

where T-wave_ER_Peak_Mag represents the T-wave ER peak magnitude of the patient and $f_2(\ )$ is a predetermined function for relating the reciprocal of the T-wave ER peak magnitude of the patient to the ventricular compliance of the patient. Depending upon the desired degree of accuracy to be achieved in relating one to the other, $f_2(\ )$ can be a first-order function, a second-order function, an exponential function, etc. The function (and any of its adjustable coefficients) can be predetermined by comparing actual values of ventricular compliance obtained via echocardiography to actual values of T-wave_ER_Peak_Mag. In one particular example, $f_2(\ )=1-\exp(-a_2*(1/T\text{-wave\_ER\_Peak\_Mag}))$ where $a_1$ is a predetermined coefficient calibrated using echocardiography. In some examples, the coefficient $a_2$ is calibrated to specifically relate the slew rate to the LV relaxation rate of the patient so that LV relaxation is thereby specifically estimated.

In some examples, the device then calculates a diastolic function metric for the patient by, e.g., calculating:

$$\text{Diastolic\_Function} = \text{Vent\_Relaxation}*k_1 + \text{Vent\_Compliance}*k_2$$

where Vent_Relaxation and Vent_Compliance are representative of the ventricular relaxation rates and the ventricular compliance values, respectively, where $k_1$ and $k_2$ are predetermined weighting constants for the relaxation rate and the compliance, respectively, and where $k_1$ and $k_2$ sum to 1. In some examples, the coefficients $k_1$ and $k_2$ are calibrated specifically for use with LV relaxation and LV compliance so that a LV diastolic function metric can thereby be estimated. Note that two of the key characteristics of diastolic dysfunction are reduced relaxation rate and reduced ventricular compliance. Hence, a metric combining these two parameters has considerable clinical utility in the management of DHF patients and the detection of patients at risk for developing DHF.

In this regard, in implementations where T-wave ER slew rate and peak magnitude are used as proxies for ventricular relaxation and ventricular compliance, the measured slew rate and peak magnitude values are merely inserted into the diastolic function equation to calculate the metric. Changes in the metric are deemed to be indicative of changes in diastolic function. For example, a decrease in Diastolic_Function is deemed to be indicative of increasing diastolic dysfunction. In implementations where actual values for ventricular relaxation and ventricular compliance are estimated for the patient (using the aforementioned coefficients $a_1$ and $a_2$), the calculated values for relaxation and compliance can instead be exploited within the diastolic function metric equation. That is, the estimated values for Ventricular Relaxation Rate and Ventricular Compliance can be inserted into the diastolic function equation rather than their proxy values (i.e. rather than slew rate and peak magnitude.) As can be appreciated, consistency should be maintained. That is, proxy values should not be mixed with numerically estimated values.

Regardless of the specific formula used by the implanted device to calculate the diastolic function metric, so long as consistency is maintained, the device can detect and track the progression of diastolic dysfunction within the patient based on the metric. In one particular example, the device evaluates the metric at least three times per day and determines if the patient has mild diastolic dysfunction, moderate diastolic dysfunction or severe diastolic dysfunction and generates warning signals accordingly. Diagnostic information is preferably recorded for clinician review. Therapy provided by the device can be controlled based on the diastolic dysfunction metric, where appropriate. For example, within some patients, it may be appropriate to initiate cardiac resynchronization therapy (CRT) in response to the detection of moderate to severe diastolic dysfunction. Depending upon the capabilities of the implantable system, other forms of therapy can also be controlled based on the diastolic function metric including neurostimulation, spinal cord stimulation, etc.

In some implementations, a diastolic function metric is not derived. Rather, the implantable device merely estimates one or both of the ventricular relaxation rate and the ventricular compliance value from the T-wave ER, records diagnostics, generates warnings, controls therapy, etc.

System and method examples of the invention are described herein below.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
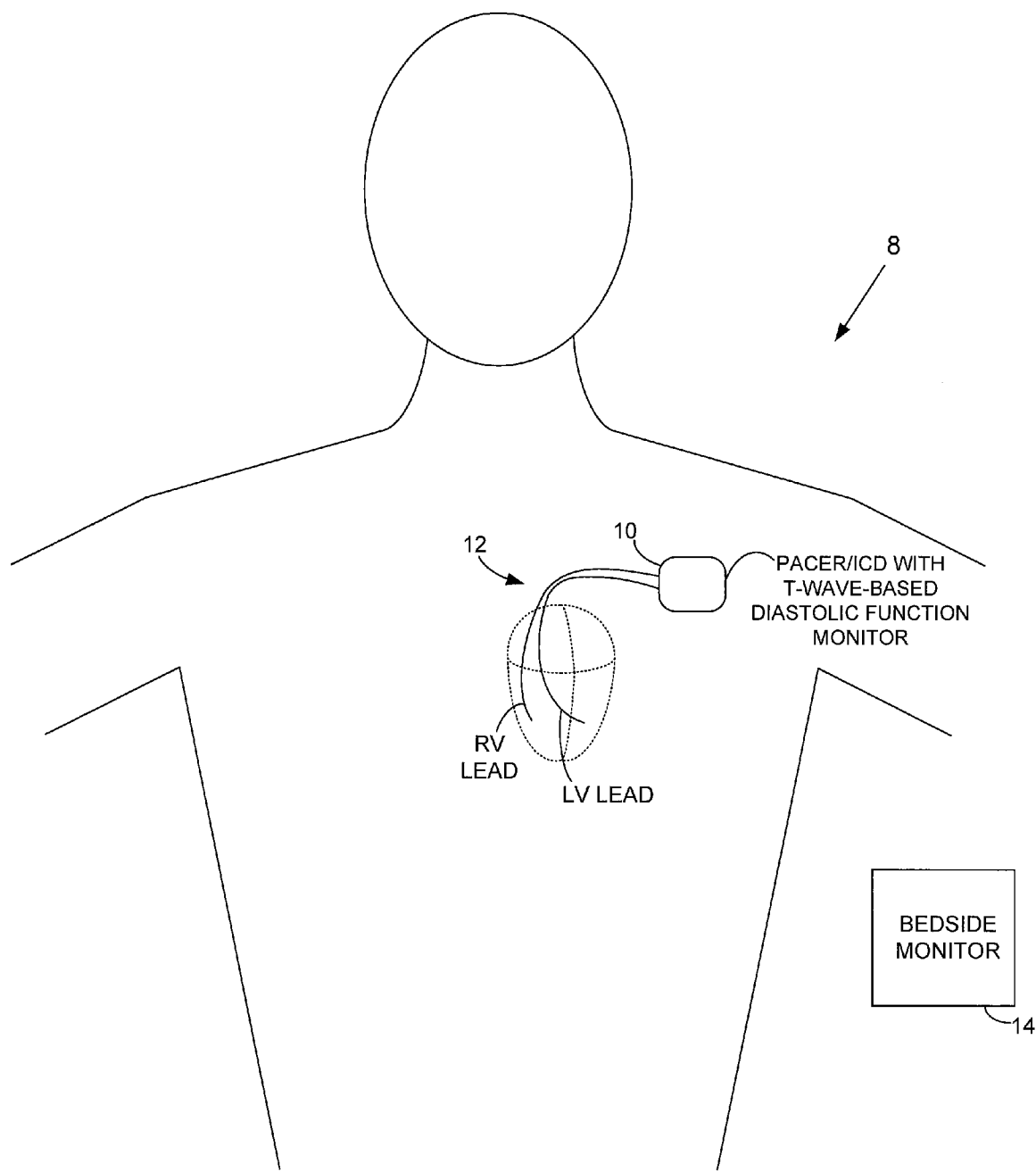
FIG. 1 illustrates pertinent components of an implantable medical system having a pacemaker or ICD capable of monitoring or evaluating diastolic function within a patient based on T-wave morphology.
Figure 6:
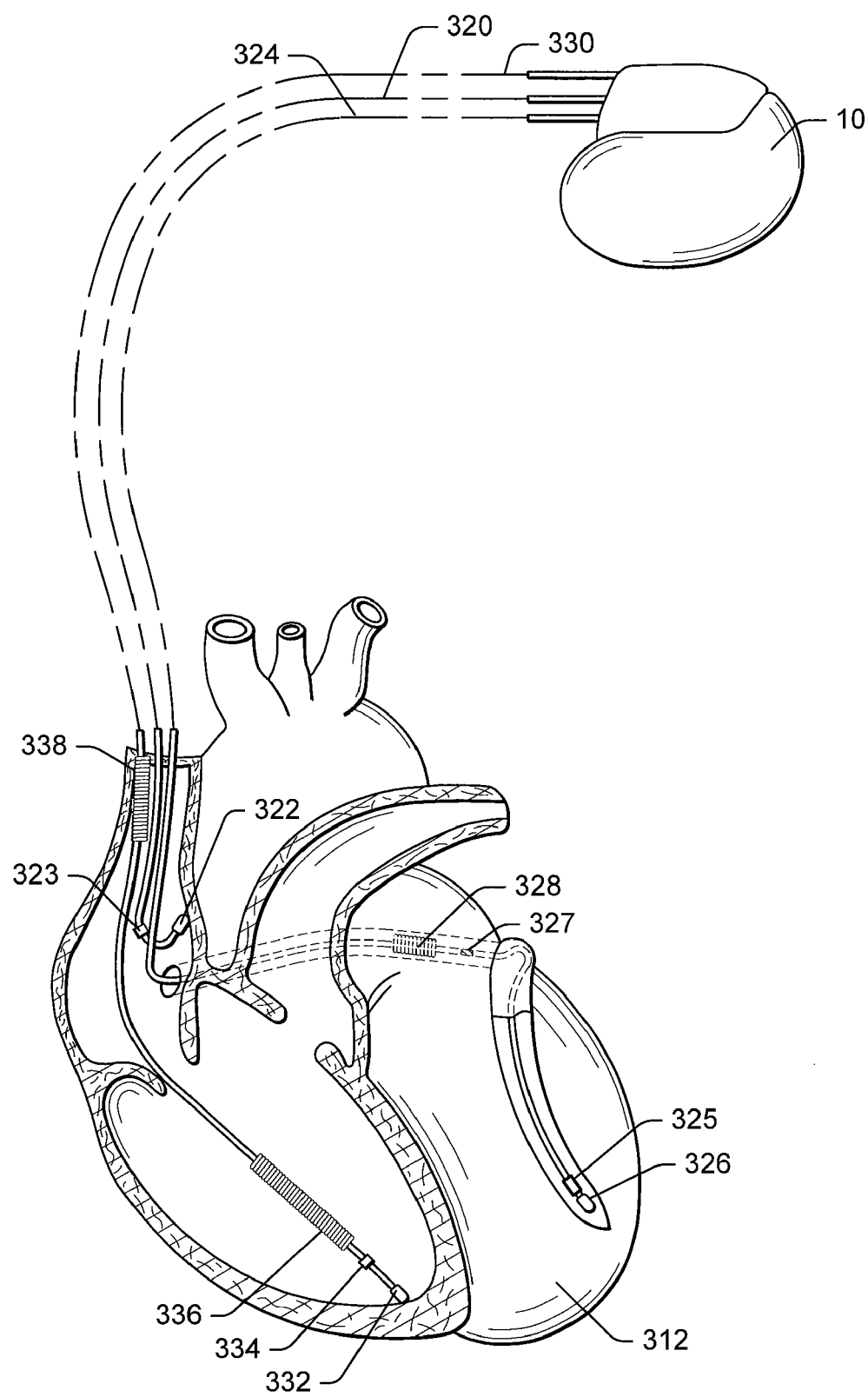
FIG. 6 is a simplified, partly cutaway view, illustrating the pacer/ICD of FIG. 1 along with at set of leads implanted into the heart of the patient.

FIG. 1 illustrates an implantable medical system 8 capable of monitoring or evaluating diastolic function based on an analysis of T-wave ER morphological parameters. To this end, medical system 8 includes a pacer/ICD 10 or other cardiac rhythm management device capable of delivering V-pulses to the ventricles via one or more cardiac sensing/pacing leads 12 implanted within the heart of the patient and further capable of sensing or detecting ER waveforms or signals generated by the V-pulse, particularly the T-wave ER. In FIG. 1, two exemplary leads are shown—an RV lead and an LV lead, in stylized form. A more complete set of leads is illustrated in FIG. 6.

Morphological parameters of the T-wave ER, particularly the peak magnitude of the T-wave ER and the post-peak maximum slew rate of the T-wave ER, are determined by the pacer/ICD and exploited to estimate ventricular relaxation and ventricular compliance, from which a diastolic function metric is derived. The diastolic function metric is tracked over time to detect and monitor diastolic dysfunction and to track the progression of diastolic dysfunction. Warning signals may be generated using an internal warning device within the pacer/ICD or a bedside monitor 14 to warn the patient of the onset or progression of any of these conditions. The internal warning device (not shown in FIG. 1) may be a vibrating device or a "tickle" voltage device that, in either case, provides perceptible stimulation to the patient to alert the patient. The bedside monitor may provide audible or visual alarm signals to alert the patient, as well as any appropriate textual or graphic displays.

Diagnostic information pertaining to diastolic function (and to any medical conditions detected therefrom such as diastolic dysfunction) may be stored within the pacer/ICD for transmission to the bedside monitor or to an external programmer (not shown in FIG. 1) for review by a clinician. The clinician then prescribes any appropriate therapies to address the condition. The clinician may also adjust the operation of the pacer/ICD to activate, deactivate or otherwise control any therapies that are automatically applied. In addition, the bedside monitor may be directly networked with a centralized computing system for immediately notifying the clinician or other caregiver of the onset of diastolic dysfunction or DHF. The centralized system may include such systems as the HouseCall™ system or the Merlin@home/Merlin.Net systems of St. Jude Medical.

The pacer/ICD may also be programmed to activate or control any pacing therapies that might be appropriate in response to DHF, such as CRT. Additionally, the pacer/ICD performs a wide variety of pacing and/or defibrillation functions such as delivering pacing is response to arrhythmias or generating and delivering shocks in response to atrial or ventricular fibrillation.

Figure 2:
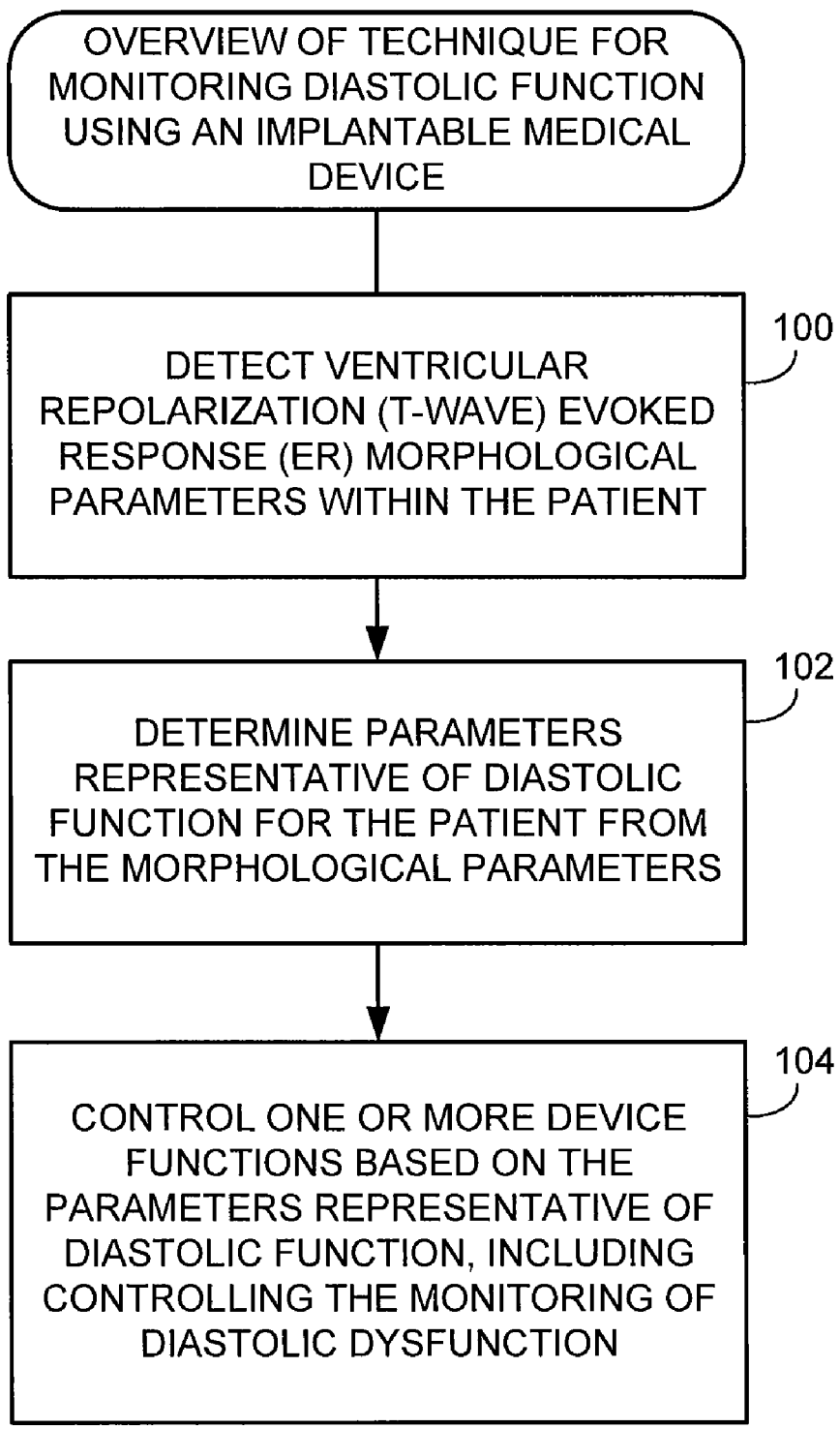
FIG. 2 is a flowchart providing an overview of the diastolic function monitoring technique performed by the system of FIG. 1.

FIG. 2 broadly summarizes the general technique for monitoring or evaluating diastolic function employed by the system of FIG. 1 or other suitably equipped systems. Beginning at step 100, the pacer/ICD detects ventricular repolarization (T-wave) ER morphological parameters within the patient. At step 102, the pacer/ICD determines parameters representative of diastolic function for the patient from the T-wave morphological parameters. As noted, ER waveforms provide information about myocardial stretch, contractility, and conduction velocity. The T-wave portion of the ER is beloved to provide information about diastolic filling and hence is useful in monitoring diastolic function. At step 104, the pacer/ICD then controls at least one device function based on the parameters representative of diastolic function, such as by controlling the storage of diagnostic data pertaining to diastolic dysfunction, controlling the generation of warning signals, and controlling therapy provided by the pacer/ICD.

Hence, FIGS. 1 and 2 provide an overview of an implantable system and method capable of monitoring or evaluating diastolic function based on T-wave ER morphology and further capable of delivering appropriate warnings, if needed, controlling therapy, etc. Embodiments may be implemented that do not necessarily perform all of these functions. For example, embodiments may be implemented that provide only for tracking diastolic function and generating diagnostic information for clinician review. In addition, systems provided in accordance with the invention need not include all the components shown in FIG. 1 such as the bedside monitor. No attempt is made herein to describe all possible combinations of components that may be provided in accordance with the general principles of the invention. Also, note that, the particular shape, size and locations of the implanted components shown in FIG. 1 are merely illustrative and may not necessarily correspond to actual implant locations. In particular, preferred implant locations for the leads are more precisely illustrated in FIG. 6.

Exemplary T-Wave-Based Diastolic Function Monitoring Technique

Figure 3:
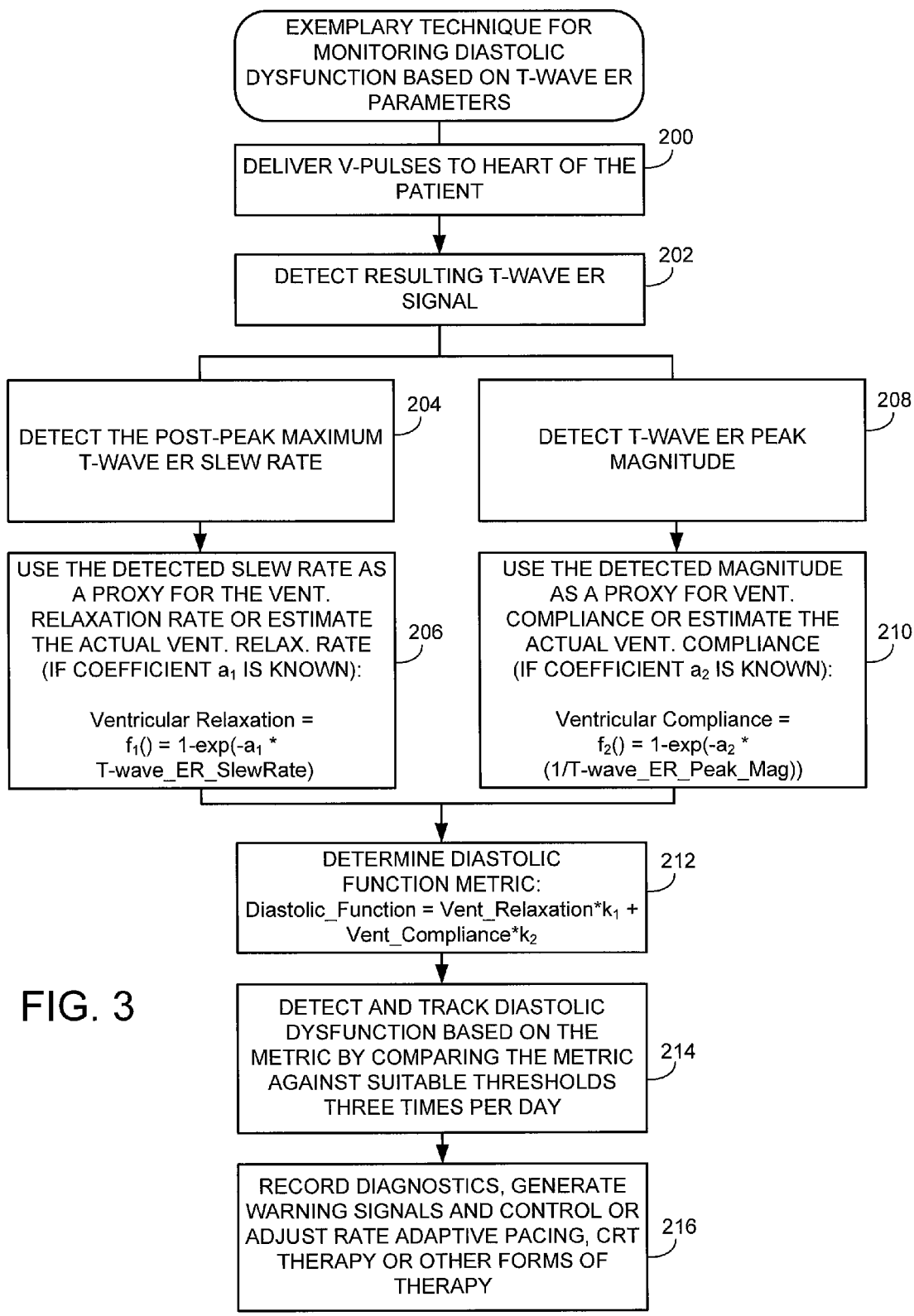
FIG. 3 illustrates an exemplary technique for monitoring diastolic function in accordance with the general technique of FIG. 2, which generates a diastolic function metric for use in monitoring diastolic dysfunction.
Figure 4:
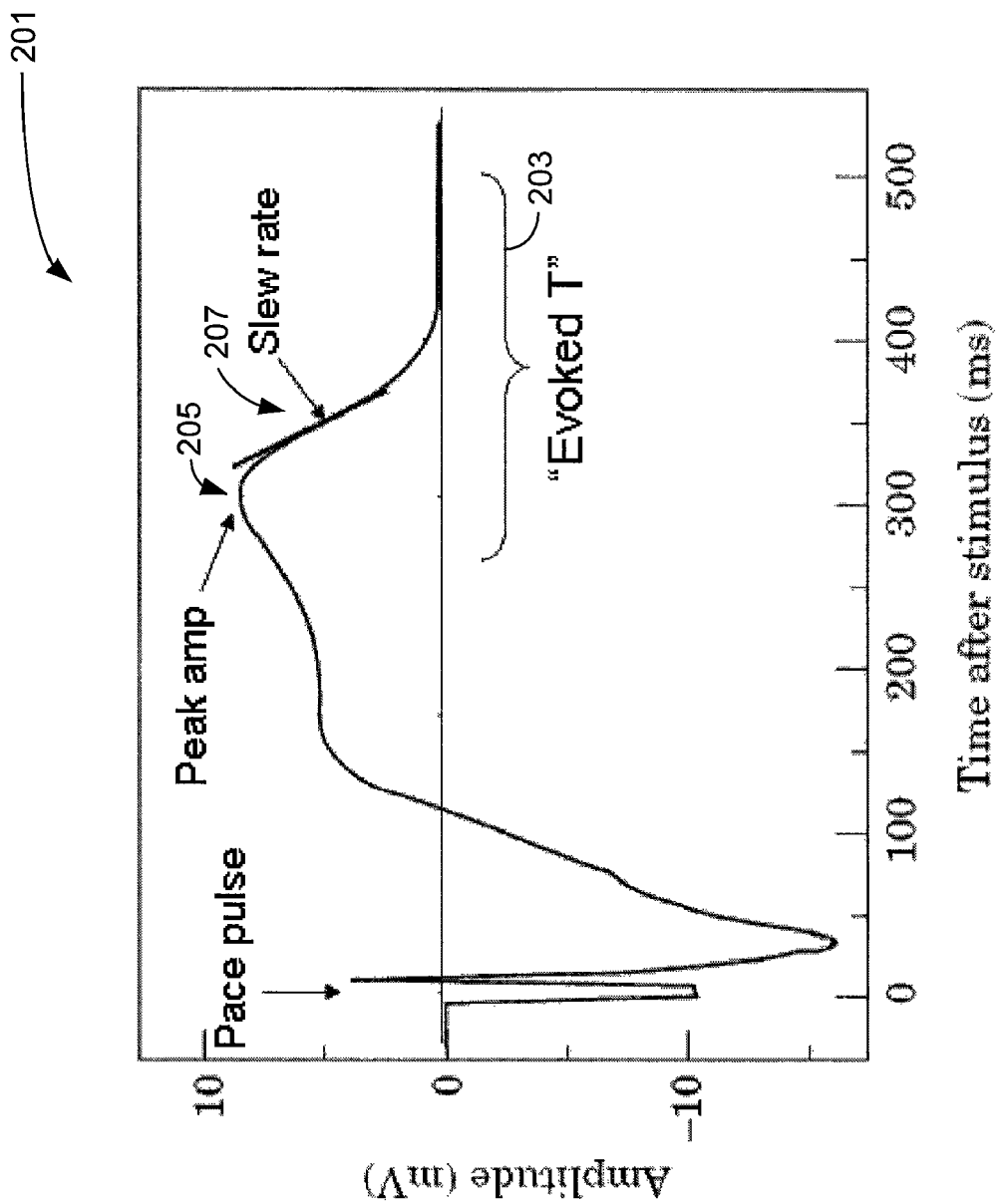
FIG. 4 is a graph illustrating particular morphological parameters of a T-wave ER, which are exploited by the technique of FIG. 3.

FIGS. 3 and 4 illustrate an exemplary technique for detecting and tracking diastolic function within a patient based on an examination of T-wave ER slew rate and peak magnitude parameters. Beginning at step 200, the pacer/ICD delivers V-pulses to the heart of the patient using pacing/sensing leads, such as by delivering pacing pulses tip-to-case via an RV tip electrode of an RV lead or via an LV tip electrode of a coronary sinus (CS) lead. The V-pulse(s) cause the ventricles of the heart of the patient to depolarize and contract producing a QRS-complex ER, which can be sensed to verify that the V-pulse was properly captured. Assuming the V-pulse was captured and the ventricles contracted, the ventricles then relax and repolarize, producing a T-wave ER. As explain above in the Summary, the "T-wave ER" refers to the repolarization portion of an evoked electrical response of the ventricles triggered by the artificial pacing pulses. Preferably, the LV T-wave ER is detected. An exemplary ER signal is shown in FIG. 4 by way of graph 201. The T-wave ER is identified via reference numeral 203.

At step 202 of FIG. 3, the pacer/ICD detects the T-wave ER signal or waveform. The delivery of V-pulses and the detection of the T-wave ERs can be performed in accordance with conventional techniques. See also the particular T-wave detection techniques set forth in: U.S. Patent Application Serial Number 2004/0077962 of Kroll, published Apr. 22, 2004, entitled "System and Method for Monitoring Blood Glucose Levels Using an Implantable Medical Device." Certain techniques described therein are particularly well suited for detecting T-waves with a high degree of accuracy to permit precise detection of morphological features of the T-wave such as its peak. See, also, U.S. Pat. No. 7,225,015, entitled "System and Method for Detecting Cardiac Ischemia Based on T-Waves Using an Implantable Medical Device", to Min et al. Certain techniques described by Min et al. help prevent P-waves from being misinterpreted as T-waves on unipolar sensing channels so as to improve the specificity with which T-waves can be detected.

At step 204, the pacer/ICD then detects the post-peak maximum T-wave ER slew rate by detecting the maximum rate of change of the magnitude of the T-wave ER following its peak. That is, the pacer/ICD detects the peak magnitude of the absolute value of the T-wave voltage signal and then evaluates the time rate of change of T-wave magnitude after the peak to detect the maximum rate of change. The maximum rate of change of the magnitude of the T-wave ER following its peak is recorded as the post-peak maximum T-wave ER slew rate. In FIG. 4, the peak of the T-wave is identified by reference numeral 205 and the maximum slew rate is identified by numeral 207. In one particular example of the technique of FIG. 3, sixteen seconds worth of cardiac signal data is collected at step 204 during LV pacing. During that interval, several heartbeats occur. The post-peak maximum T-wave ER slew rate for each individual heartbeat is detected on a beat-by-beat basis and stored. The values are then averaged.

At step 206, the pacer/ICD then uses the post-peak maximum T-wave ER slew rate (averaged or otherwise) as a proxy for ventricular relaxation or, if a suitable conversion function has been calibrated for the patient., the pacer/ICD can numerically estimate the ventricular relaxation rate for the patient.

That is, in one example of the implementation of FIG. 3, the pacer/ICD merely uses the slew rate as a proxy for ventricular relaxation. In this regard, it is believed that a prolonged evoked T-wave is generally correlated with a relatively long ventricular relaxation period. The longer the ventricular relaxation period, the slower the relaxation rate. Moreover, the more prolonged the evoked T-wave, the slower the maximum post-peak slew rate of the T-wave ER. Accordingly, a relatively slow maximum post-peak slew rate for the T-wave ER thereby corresponds with a relatively slow relaxation rate. Conversely, a relatively fast maximum post-peak slew rate for the T-wave ER thereby corresponds with a relatively fast relaxation rate.

Hence, these slew rates can be used as a proxy for ventricular relaxation rate. If the slew rate is found to increase over time within the patient, then the ventricular relaxation rate is deemed to have increased (i.e. improved) within the patient. If the slew rate decreases over time, then ventricular relaxation is deemed to have decreased (i.e. worsened). Slew rate values may be stored for later review by a clinician or, as will be explained below, the slew rates can be used to calculate a diastolic function metric, which is stored.

In other examples of the implementation of FIG. 3, the pacer/ICD instead estimates or calculates an actual numerical value for ventricular relaxation rate of the patient (which pertains to pressure decay and is represented in mmHg/sec) by exploiting a predetermined conversion function $f_1(\ )$ for the patient, assuming that function has already been determined and calibrated for the patient. That is, the pacer/ICD estimates the actual ventricular relaxation rate for the patient by calculating:

$$\text{Ventricular Relaxation Rate} = f_1(T\text{-wave\_ER\_SlewRate})$$

where T-wave_ER_SlewRate represents the maximum post-peak T-wave ER slew rate of the patient and $f_1(\ )$ is the predetermined function for converting the maximum post-peak T-wave ER slew rate of the patient to the ventricular relaxation rate of the patient. As noted above, depending upon the desired degree of accuracy to be achieved in relating one to the other, $f_1(\ )$ can be a first-order function, a second-order function, an exponential function, etc. The function (and any of its adjustable coefficients) can be predetermined by comparing actual values of ventricular relaxation rates obtained via echocardiography to actual values of T-wave_ER_SlewRate.

In one example, $f_1(\ ) = 1 - \exp(-a_1 * T\text{-wave\_ER\_SlewRate})$ where $a_1$ is a predetermined coefficient. This particular function is generally preferred since the asymptotes of the exponential function limit the range of the resulting Ventricular Relaxation Rate value. The constant, $a_1$, can be calibrated with echocardiography during which real ventricular relaxation rate values are measured. Note that, if a linear function is used for $f_1(\ )$, a very high slew rate value might produce unrealistic values for relaxation rate and so a purely linear function relating slew rate to ventricular relaxation rate is generally not recommended. Note also that, in some examples, the coefficient $a_1$ is calibrated to specifically relate the slew rate to the LV relaxation rate of the patient so that LV relaxation is thereby specifically estimated.

To calibrate the exponential function, the patient visits a clinic to have their LV relaxation rate computed by echocardiography, while T-wave ERs are detected and their maximum post-peak slew rates are measured. Preferably, relaxation rate values and corresponding slew rate values are obtained for different heart rates to provide multiple point calibration to increase accuracy. The clinically measured values for relaxation and max post-peak slew rate are then numerically processed (via, e.g. linear regression) to determine the value for the coefficient $a_1$ for the patient, which is then stored in the pacer/ICD of the patient. With this value, the pacer/ICD can then estimate actual ventricular relaxation rates within the patient from the measured maximum post-peak slew rates. Periodic recalibration may be appropriate. It should be understood, though, that these calibration steps are only performed if a numerical value for ventricular relaxation rate is desired. For many applications, it is instead sufficient merely to use the measured post-peak maximum slew rate as a proxy for ventricular relaxation by, e.g., using the slew rate values to calculate a diastolic function metric.

Concurrently with step 204, the pacer/ICD at step 208 also detects the T-wave ER peak magnitude by tracking the absolute value of the voltage signal of the T-wave ER. As with the detection of slew rate, sixteen seconds worth of cardiac signal data may be collected at step 208 during ventricular pacing to obtain an averaged value for peak magnitude.

At step 210, the pacer/ICD then uses the peak magnitude (averaged or otherwise) as a proxy for ventricular compliance or, if a suitable conversion function has been calibrated for the patient, the pacer/ICD can numerically estimate the ventricular compliance for the patient.

That is, similar to slew rate/relaxation rate, the pacer/ICD can use the peak magnitude of the T-wave ER as a proxy for ventricular compliance. In this regard, it is believed that the peak magnitude of the T-wave ER is generally correlated with the degree of stiffness of the ventricles and hence is also generally correlated with ventricular compliance (wherein greater compliance corresponds to less stiffness.) Accordingly, a relatively low peak magnitude for the T-wave ER corresponds with relatively stiff ventricles and poor compliance. Conversely, a relatively high peak magnitude for the T-wave ER corresponds with a relatively stretchable ventricles and better compliance.

Hence, peak magnitude can be used as a proxy for ventricular compliance. If the peak magnitude is found to increase over time within the patient, then ventricular compliance is deemed to have improved within the patient. If the peak magnitude decreases over time, then ventricular compliance is deemed to have decreased (i.e. worsened). Peak magnitude values may be stored for later review by a clinician or, as will be explained below, the peak magnitude values can be used to calculate a diastolic function metric.

In other examples, the pacer/ICD estimates or calculates an actual numerical value for ventricular compliance (in units of deltaV/deltaP, or "change in volume (ml)"/"change in pressure (mmHg)") by exploiting the predetermined conversion function $f_2(\ )$ for the patient, assuming that function has already been determined and calibrated for the patient. That is, the pacer/ICD estimates the actual ventricular compliance for the patient by calculating:

$$\text{Ventricular Compliance} = f_2(1/\text{T-wave\_ER\_Peak\_Mag}),$$

where T-wave_ER_Peak_Mag represents the T-wave ER peak magnitude of the patient and $f_2(\ )$ is a predetermined function for relating the reciprocal of the T-wave ER peak magnitude of the patient to the ventricular compliance of the patient. As noted above, depending upon the desired degree of accuracy to be achieved in relating one to the other, $f_2(\ )$ can be a first-order function, a second-order function, an exponential function, etc. The function (and any of its adjustable coefficients) can be predetermined by comparing actual values of ventricular compliance obtained via echocardiography to actual values of T-wave_ER_Peak_Mag.

In one example, $f_2(\ ) = 1 - \exp(-a_2 * (1/\text{T-wave\_ER\_Peak\_Mag}))$ where $a_2$ is a predetermined coefficient. This particular function is generally preferred since the asymptotes of the exponential function limit the range of the resulting Ventricular Compliance value. The constant, $a_2$, can be calibrated with echocardiography during which real ventricular compliance values are measured. Note that, as with $f_1(\ )$, if a linear function is used for $f_2(\ )$, a very high peak magnitude might produce unrealistic values for compliance and so a purely linear function relating peak magnitude to ventricular compliance is generally not recommended. Note also that, in some examples, the coefficient $a_2$ is calibrated to specifically relate the peak magnitude to LV compliance for the patient so that LV compliance is thereby specifically estimated.

As with the calibration of ventricular relaxation discussed above, the patient can visit a clinic to have their ventricular compliance computed by echocardiography, while T-wave ERs are detected and their peak magnitudes measured. Preferably, ventricular compliance values and corresponding peak magnitude values are obtained for different heart rates to provide multiple point calibration to increase accuracy. The clinically measured values for compliance and peak magnitude are then numerically processed (again using, e.g. linear regression) to determine the value for the coefficient $a_2$ for the patient, which is then stored in the pacer/ICD of the patient. With this value, the pacer/ICD can then estimate actual ventricular compliance values within the patient from the measured peak magnitude of the T-wave ER. Periodic recalibration may again be appropriate. It should again be understood that the calibration steps are only performed if a numerical value for ventricular compliance rate is desired. For many applications, it is sufficient use peak magnitude as a proxy for ventricular compliance by, e.g., using the peak magnitude values to calculate a diastolic function metric.

At step 212, the pacer/ICD can then determine a diastolic function metric:

$$\text{Diastolic\_Function} = \text{Vent\_Relaxation} * k_1 + \text{Vent\_Compliance} * k_2$$

where Vent_Relaxation and Vent_Compliance are representative of the ventricular relaxation rates and the ventricular compliance values, respectively, where $k_1$ and $k_2$ are predetermined weighting constants for the relaxation rate and the compliance, respectively, and where $k_1$ and $k_2$ sum to 1. In some examples, the coefficients $k_1$ and $k_2$ are calibrated specifically for use with LV relaxation and LV compliance so that a LV diastolic function metric can thereby be estimated. Typically, values for $k_1$ and $k_2$ are programmed in advance by the physician or clinician based on his or her opinion about the relative weight that should be given to ventricular relaxation rates, relative to ventricular compliance, when assessing diastolic function. In some examples, $k_1$ and $k_2$ will both be set to 0.5.

Further with regard to the calculation of the Diastolic_Function metric, in implementations of FIG. 3 where the T-wave ER slew rate and peak magnitude (detected at steps 204 and 208) are to be used as proxies for ventricular relaxation and ventricular compliance, then the measured slew rate and peak magnitude values are merely inserted into the diastolic function equation to calculate the metric. Changes in the metric are then deemed to be indicative of changes in diastolic function. For example, a decrease in the Diastolic_Function metric is deemed to be indicative of increasing diastolic dysfunction.

In implementations of FIG. 3 where actual values for ventricular relaxation and ventricular compliance are estimated for the patient using the aforementioned equations, these relaxation and compliance values can instead be exploited within the diastolic function metric equation. That is, the estimated values for Ventricular Relaxation Rate and Ventricular_Compliance can be inserted into the diastolic function equation. In either case, a metric value is thereby generated that is representative of diastolic function within the patient and which can then be tracked over time. (As can be appreciated, consistency should be maintained. That is, proxy values should not be mixed with numerically estimated values while calculating the metric.)

Figure 5:
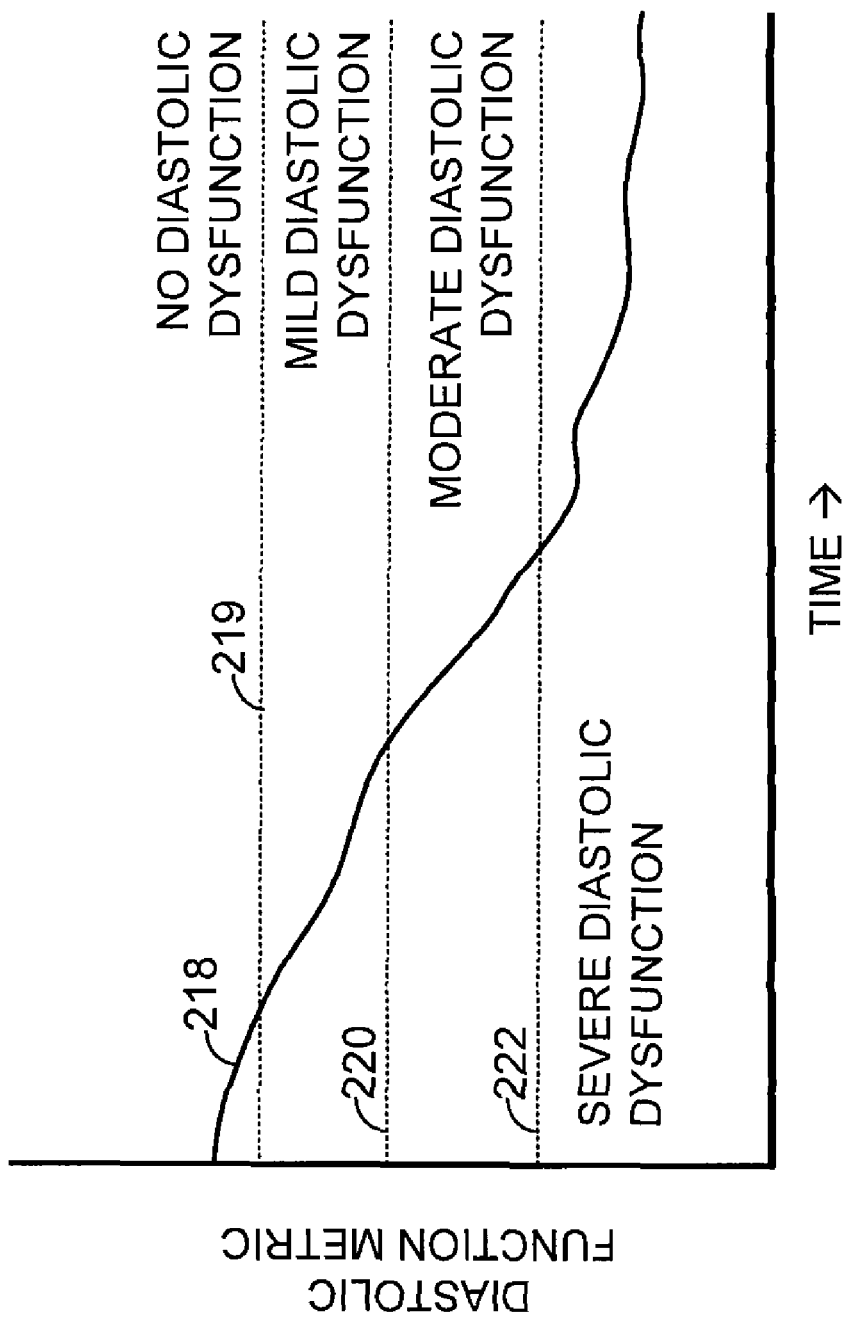
FIG. 5 is a graph illustrating an exemplary diastolic function metric generated by the technique of FIG. 3, and particularly illustrating thresholds indicative of mild diastolic dysfunction, moderate diastolic dysfunction and severe diastolic dysfunction.

At step 214, the pacer/ICD then detects and tracks (i.e. trends) diastolic dysfunction based on the metric by, e.g., comparing the metric against suitable threshold values three times per day. This is illustrated in FIG. 5 by way of diastolic function metric curve 218 and thresholds 219, 220 and 222. As the metric value decreases over time, threshold 219 (indicative of the onset of mild diastolic dysfunction) is first crossed, then threshold 220 (indicative of the moderate diastolic dysfunction) is crossed, then threshold 222 (indicative of severe diastolic dysfunction) is crossed. In one example, the threshold values are determined for the patient relative to a baseline value for the metric calculated within the patient following device implant. That is, under the supervision of a clinician, the pacer/ICD calculates an initial metric value within the patient and stores that value as a baseline value within device memory. The pacer/ICD then sets the thresholds relative to the baseline value (subject to clinician review). In this manner, changes relative to the patient baseline are tracked. These threshold values are merely exemplary. Clinical research can be performed on patient populations to specify preferred or optimal thresholds values based on pre-DHF and DHF patients. Also, as can be appreciated, separate thresholds can also be specified for any of the individual values measured or calculated by the device for comparison (e.g. post-peak maximum T-wave ER slew rate, T-wave ER peak magnitude, ventricular relaxation rate, ventricular compliance.)

At step 216, the pacer/ICD records diagnostic information, generates warning signals and adjusts or controls therapy, where appropriate. For example, the metric value may be stored for clinician review along with the aforementioned slew rate and peak magnitude values. If actual values for the ventricular relaxation rate and ventricular compliance are calculated, these values can be stored as well. Warnings can be generated upon crossing the aforementioned thresholds indicative of progression of diastolic dysfunction. Optionally, any therapies approached for DHF can be activated or controlled by the pacer/ICD based on the metric. As noted, in some patients it may be appropriate to activate CRT in response to the detection of diastolic dysfunction (if the device is so equipped.) Briefly, CRT seeks to normalize asynchronous cardiac electrical activation and resultant asynchronous contractions associated with DHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

Also, at step 216, it may be appropriate to control rate adaptive pacing in response to diastolic dysfunction to selectively activate/deactivate such pacing or to adjust any rate adaptive pacing control parameters. Depending upon the capabilities of the implantable system, other forms of therapy can also be controlled based on the diastolic function metric including neurostimulation, spinal cord stimulation, etc.

What have been described are various techniques for monitoring or evaluating diastolic function are related parameters and conditions. For the sake of completeness, a detailed description of an exemplary pacer/ICD for performing these techniques will now be provided. However, principles of invention may be implemented within other pacer/ICD implementations or within other implantable devices such as stand-alone diastolic function monitoring devices, CRT devices or CRT-D devices. Furthermore, although examples described herein involve processing of diastolic function data by the implanted device itself, some operations may be performed using an external device, such as a bedside monitor, device programmer, computer server or other external system. For example, recorded T-wave ER data may be transmitted to the external device, which processes the data to evaluate diastolic function. Processing by the implanted device itself is preferred as that allows the device to detect the onset of diastolic dysfunction and to issue prompt warnings.

Exemplary Pacer/ICD

FIG. 6 provides a simplified block diagram of the pacer/ICD, which is a dual-chamber stimulation device capable of treating both fast and slow arrhythmias with stimulation therapy, including cardioversion, defibrillation, and pacing stimulation, as well as capable of performing the diastolic function monitoring or evaluating functions described above. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 6, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 7:
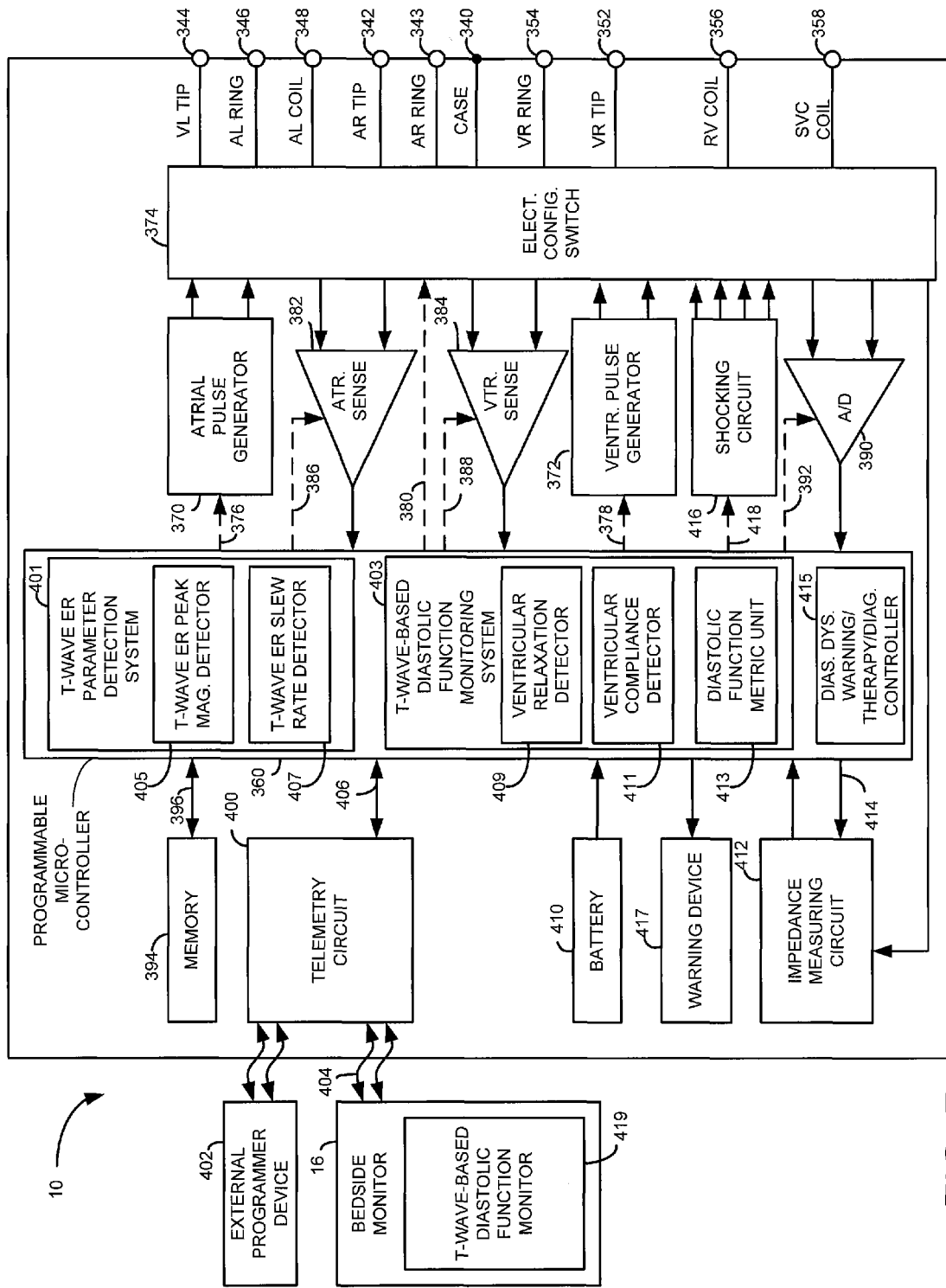
FIG. 7 is a functional block diagram of the pacer/ICD of FIG. 6, illustrating basic circuit elements that provide cardioversion, defibrillation and/or pacing stimulation in the heart and particularly illustrating components for monitoring or evaluating diastolic function using the techniques of FIGS. 2-5.

A simplified block diagram of internal components of pacer/ICD 10 is shown in FIG. 7. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned diastolic function monitoring functions.

The housing 340 for pacer/ICD 10, shown schematically in FIG. 7, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal (AR TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal (AL RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 7, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the aforementioned thresholds as well as pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 7. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, pacer/ICD 10 is preferably capable of high voltage therapy and appropriate batteries.

As further shown in FIG. 7, pacer/ICD 10 is shown as having an impedance measuring circuit 412 which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to monitoring or evaluating diastolic function. In particular, the microcontroller includes a T-wave ER parameter detection system 401 operative to detect ventricular repolarization ER morphological parameters within the patient. Also included is a T-wave-based diastolic function monitoring system 403 operative to determine parameters representative of diastolic function for the patient from the ventricular repolarization ER morphological parameters.

As shown, the T-wave ER parameter detection system 401 includes: a T-wave ER peak amplitude detector 405 operative to detect a T-wave ER peak magnitude within the patient and a T-wave ER slew rate detector 407 operative to detect a post-peak maximum T-wave ER slew rate within the patient. The T-wave-based diastolic function monitoring system 403 includes: a ventricular relaxation rate detector 409 operative to determine the ventricular relaxation rate for the patient based on the post-peak maximum T-wave ER slew rate; a ventricular compliance detector 411 operative to determine a ventricular compliance value for the patient based on the T-wave ER peak magnitude; and a diastolic function metric determination unit 413 operative to determine a diastolic function metric value for the patient from the ventricular relaxation and compliance values (detected by detectors 509 and 511) or directly from the ventricular repolarization ER morphological parameters detected by system 401, or a combination of both.

A diastolic dysfunction warning/therapy/diagnostics controller 415 controls the detection of diastolic dysfunction based on the diastolic function metric (or on individual morphological parameters such as post-peak maximum T-wave ER slew rate.) Controller 415 also controls the generation of diagnostic data and warning signals based on the diastolic function metric (or other values). The diagnostic data is stored within memory 394. Warning signals may be relayed to the patient via internal warning device 417 or via bedside monitor 16 or programmer 402.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller. Note also that, in some implementations, the aforementioned ventricular relaxation rate detector and the ventricular compliance detector are not components of a diastolic function monitoring system but operate independently.

When used in conjunction with an external system such as a bedside monitor, the external system can perform some of the diastolic monitoring functions, such as by analyzing T-wave ER data transmitted by the pacer/ICD. This is shown by way of T-wave-based diastolic function monitor 419 of the bedside monitor. In other words, not all of the functions need be performed by the pacer/ICD but functions can be distributed among various systems, some implanted within the patient, others external.

What have been described are various systems and methods for use with a pacer/ICD or an external system used in conjunction with a pacer/ICD. However, principles of the invention may be exploiting using other implantable medical systems. Thus, while the invention has been described with reference to particular exemplary embodiments, modifications can be made thereto without departing from the scope of the invention.

What is claimed is:

1. A method for use with an implantable medical device for implant within a patient, the method comprising:
  detecting ventricular repolarization evoked response (ER) morphological parameters within the patient;
  determining parameters representative of diastolic function for the patient from the ventricular repolarization ER morphological parameters; and
  controlling at least one device function based on the parameters representative of diastolic function.

2. The method of claim 1 wherein detecting ventricular repolarization ER morphological parameters includes detecting a maximum post-peak T-wave ER slew rate.

3. The method of claim 2 wherein detecting the maximum post-peak T-wave ER slew rate includes detecting the peak of the T-wave ER and then determining a maximum rate of change of a magnitude of the T-wave ER following the peak.

4. The method of claim 2 wherein determining parameters representative of diastolic function includes employing the maximum post-peak T-wave ER slew rate as a proxy for a ventricular relaxation rate of the patient.

5. The method of claim 2 wherein determining parameters representative of diastolic function includes determining a ventricular relaxation rate of the patient from the maximum post-peak T-wave ER slew rate.

6. The method of claim 5 wherein determining the ventricular relaxation rate from the maximum post-peak T-wave ER slew rate includes estimating the ventricular relaxation rate based on a predetermined correlation between the maximum post-peak T-wave ER slew rate and the ventricular relaxation rate of the patient.

7. The method of claim 6 wherein estimating the ventricular relaxation rate includes calculating:

$$\text{Ventricular Relaxation Rate} = f_1(\text{T-wave\_ER\_SlewRate})$$

where T-wave_ER_SlewRate represents the maximum post-peak T-wave ER slew rate of the patient and $f_1()$ is a predetermined function relating the maximum post-peak T-wave ER slew rate with the ventricular relaxation rate of the patient.

8. The method of claim 1 wherein detecting ventricular repolarization ER morphological parameters includes detecting a T-wave ER peak magnitude.

9. The method of claim 8 wherein determining parameters representative of diastolic function includes employing the T-wave ER peak magnitude as a proxy for a ventricular compliance of the patient.

10. The method of claim 8 wherein determining parameters representative of diastolic function for the patient includes determining ventricular compliance for the patient from the T-wave ER peak magnitude.

11. The method of claim 10 wherein determining ventricular compliance values from the T-wave ER peak magnitude includes estimating ventricular compliance based on a predetermined correlation between T-wave ER peak magnitude and ventricular compliance within the patient.

12. The method of claim 11 wherein estimating the ventricular compliance based on a predetermined correlation between the T-wave ER peak magnitude and the ventricular compliance includes calculating:

$$\text{Ventricular Compliance} = f_2(1/\text{T-wave\_ER\_Peak\_Mag})$$

where T-wave_ER_Peak_Mag represents the T-wave ER peak magnitude of the patient and $f_2()$ is a predetermined conversion function relating the T-wave ER magnitude with the ventricular compliance within the patient.

13. The method of claim 1 wherein determining parameters representative of diastolic function includes determining ventricular relaxation rates and ventricular compliance values for the patient and wherein the method further includes calculating a diastolic function metric for the patient from the ventricular relaxation rates and the ventricular compliance values.

14. The method of claim 13 wherein calculating a diastolic function metric from the ventricular relaxation rates and the ventricular compliance values includes calculating:

$$\text{Diastolic\_Function} = \text{Vent\_Relaxation} * k_1 + \text{Vent\_Compliance} * k_2$$

where Vent_Relaxation and Vent_Compliance are representative of the ventricular relaxation rates and the ventricular compliance values, respectively, where $k_1$ and $k_2$ are predetermined weighting constants for the relaxation rate and the compliance respectively, and where $k_1$ and $k_2$ sum to 1.

15. The method of claim 14 further including monitoring diastolic dysfunction within the patient based on the diastolic function metric.

16. The method of claim 15 wherein monitoring diastolic dysfunction within the patient based on the diastolic function metric includes detecting a change in the metric from an initial baseline value derived for the patient.

17. The method of claim 15 wherein monitoring diastolic dysfunction includes detecting one or more of mild diastolic dysfunction, moderate diastolic dysfunction and severe diastolic dysfunction.

18. The method of claim 13 further including controlling the delivery of therapy provided by the device based on the diastolic function metric.

19. The method of claim 1 further including controlling the delivery of therapy provided by the device based on any of the parameters representative of diastolic function.

20. The method of claim 1 further including controlling rate adaptive pacing provided by the device based on any of the parameters representative of diastolic function.

21. A system for use with an implantable medical device for implant within a patient, the system comprising:
  a ventricular repolarization evoked response (ER) morphological parameter detection unit operative to detect ventricular repolarization ER morphological parameters within the patient; and a diastolic function determination unit operative to determine parameters representative of diastolic function for the patient from the ventricular repolarization ER morphological parameters.

22. The system of claim 21 further including a controller operative to control at least one device function based on the parameters representative of diastolic function.

23. The system of claim 21 wherein the ventricular repolarization ER morphological parameter detection unit includes a T-wave ER slew rate detection unit operative to detect a maximum post-peak T-wave ER slew rate within the patient, and wherein the diastolic function determination unit includes a ventricular relaxation rate detection unit operative to determine the ventricular relaxation rate for the patient based on the T-wave ER slew rate.

24. The system of claim 21 wherein the ventricular repolarization ER morphological parameter detection unit includes a T-wave ER peak magnitude detection unit operative to detect a peak T-wave ER magnitude within the patient, and wherein the diastolic function determination unit includes a ventricular compliance detection unit operative to determine a ventricular compliance value for the patient based on the peak T-wave ER magnitude.

25. The system of claim 21 wherein the diastolic function determination unit includes a diastolic function metric determination unit operative to determine a diastolic function metric value for the patient from the ventricular repolarization ER morphological parameters.

26. The system of claim 25 further including a controller operative to control the delivery of warnings provided by the device based on the diastolic function metric.

27. A method for use with an implantable medical device for implant within a patient, the method comprising:
  detecting ventricular repolarization evoked response (ER) morphological parameters within the patient; and
  monitoring diastolic function within the patient using the ventricular repolarization ER morphological parameters.

* * * * *